United States Patent [19]

Hintz et al.

[11] Patent Number: 5,780,390
[45] Date of Patent: Jul. 14, 1998

[54] AGRICULTURAL SPRAY ADJUVANT COMPRISING COCONUT DIETHANOLAMIDE AND POLYALKYLENE GLYCOL

[75] Inventors: Sherwin David Hintz; Julio Jose Bordas, both of Miami, Fla.

[73] Assignee: GB Biosciences Corporation, Wilmington, Del.

[21] Appl. No.: 562,521

[22] Filed: Nov. 22, 1995

[51] Int. Cl.$^6$ .................... A01N 25/30; B01F 17/16
[52] U.S. Cl. .................... 504/116; 424/405; 514/525; 252/357
[58] Field of Search .................... 504/116; 424/405; 252/357; 514/525

[56] References Cited

U.S. PATENT DOCUMENTS

| | | | |
|---|---|---|---|
| 4,867,972 | 9/1989 | Girardeau et al. | 424/81 |
| 4,933,371 | 6/1990 | Hink et al. | 514/739 |
| 4,975,425 | 12/1990 | Barnett, Jr. | 514/119 |
| 4,997,592 | 3/1991 | Woogerd | 252/354 |
| 5,112,515 | 5/1992 | Buxton et al. | 252/106 |
| 5,294,644 | 3/1994 | Login et al. | 514/698 |

*Primary Examiner*—S. Mark Clardy
*Attorney, Agent, or Firm*—Thompson Hine & Flory LLP

[57] ABSTRACT

An agricultural spray adjuvant composition that can be added to an agricultural spray to enhance the deposition of the agricultural spray by preventing evaporation, reducing surface tension, stabilizing dynamic surface tension and enhancing stickability comprising coconut acid diethanolamide and a method employing the same.

17 Claims, No Drawings

AGRICULTURAL SPRAY ADJUVANT COMPRISING COCONUT DIETHANOLAMIDE AND POLYALKYLENE GLYCOL

The present invention relates to a composition which can be added to an agricultural spray to enhance spray deposition of the active agent and to many agricultural spray compositions and a method employing the same.

Agricultural compositions such as fungicides and other pesticides are frequently applied to crops by aerial spraying. The effectiveness of these agricultural agents therefor is a function of the activity of the active agent, spraying conditions, and the retention of the agent on the surface of the plant. A number of factors affect the ability of a droplet of a spray containing an agricultural agent to stick to a plant. Some of these factors are discussed by Spillman, John J. "Spray Inspection, Retention and Adhesion: an Introduction to Basic Characteristics", Pestic. Sci., 1984, 15, 97-106. As Spillman points out, the factors which influence whether a droplet remains on or bounces off a surface are complex. Smaller droplets are generally retained better than larger droplets and droplets having a lower surface tension and stable dynamic surface tension are retained better than droplets having higher surface tensions. Another factor that can influence spray deposition is evaporation from the droplet as the droplet falls through the air. If a droplet dries to the extent that it behaves more like a solid particle than a liquid one, it will tend to bounce off the leaf surface instead of sticking to it. It will also tend to be carried off by the wind like a dust particle which makes it more difficult to control its application to the targeted surface.

SUMMARY OF THE INVENTION

The present invention provides a spray adjuvant that enhances the deposition of an agricultural spray by preventing evaporation, reducing surface tension, stabilizing dynamic surface tension and enhancing stickability. The adjuvant of the present invention comprises coconut acid diethanolamide. The fatty acid diethanolamide enhances the ability of the spray droplet to retain water. The diethanolamide can be used alone but it is typically combined with other hydrophilic agents. In accordance with a specific embodiment of the invention, the adjuvant comprises a combination of coconut diethanolamide, a polyalkylene oxide, and glycerin.

One manifestation of the invention is a method for applying agricultural agents to crops which comprises spraying from an aircraft or a non-aerial applicator a composition which comprises water, coconut diethanolamide and an agricultural agent selected from a group consisting of herbicides, insecticides and fungicides. Preferably, the composition is applied to crops by spraying from an aircraft.

Another manifestation of the invention is an optimal spray adjuvant formulation for addition to an agricultural spray dilution to enhance its deposition and retention on the crop foliage when applied by aerial or non-aerial spraying which consists essentially of an aqueous solution of coconut diethanolamide and one or more hydrophilic agents. Preferably, the spray adjuvant is for addition to an agricultural composition to enhance aerial spraying deposition.

Another manifestation of the invention is a composition for aerial or non-aerial spray application to crops comprising water, an agricultural agent, and coconut diethanolamide, said diethanolamide being present in an amount of about 1.7 to 16.7% by volume. Preferably, the composition is for aerial spray application to crops.

DETAILED DESCRIPTION OF THE INVENTION

Coconut diethanolamide is commercially available. The coconut diethanolamide is generally present in equilibrium with some coconut acid (i.e. 13%) and diethanolamine (i.e. 25%) in these formulations. In this disclosure, the amounts of diethanolamide represent the total amount of diethanolamide, acid and amine in the formulation. One source for the diethanolamide is Stepan Company under the tradename Ninol 11-CM.

In accordance with the invention, the adjuvant is formulated such that coconut diethanolamide is added to the agricultural spray dilution in an amount of about 1.7 to 16.7% by volume. The adjuvant itself, i.e., the pre-mix as formulated for addition to the spray, can be formulated in any concentration that is convenient for admixing with the spray. Factors to consider in determining the concentration of the pre-mix include viscosity and solution properties.

In the spray, coconut diethanolamide functions as a humectant and as a spreading, binding or sticking agent. To further enhance deposition, it is desirable to use one or more hydrophilic agents with the diethanolamide. The hydrophilic agent can further reduce surface tension and stabilize dynamic surface tension of the spray dilution which enhances the droplet's ability to spread upon contacting the leaf. Because the agent is hydrophilic, it also complements and does not detract from the humectant properties of the coconut diethanolamide. Highly hydrophilic agents are also beneficial in reducing water loss from the droplet and in enhancing spray deposition.

One or more hydrophilic agents will generally be present in the spray dilution in an amount of about 1.3 to 13.3% by volume. In the adjuvant, one or more hydrophilic agents will typically be present in an amount of 20 to 100 parts per 100 parts by weight of the diethanolamide.

A preferred hydrophilic agent is a polyalkylene glycol such as polyethylene glycol or polypropylene glycol. The molecular weight of these glycols can range from about 100 to 1000. While it is desirable to use a polyalkylene glycol in the spray, those skilled in the art will recognize easily that other hydrophilic agents can be used to reduce surface tension without detracting from the humectant effect of the diethanolamide. Other useful hydrophilic agents include: ethoxylated dodecyl benzene sulfonic acid (DDBSA), polyethylene glycols 100, 200, 400, 600 and 1000, ethoxylated nonylphenols and glycerin.

More preferably, a preferred hydrophilic agent is polyethylene glycol 200. Polyethylene glycol 200 will generally be present in the spray dilution in an amount of about 0.6 to 6.6% by volume and will be present in the adjuvant in an amount of about 2 to 20% by volume. More preferably, the polyethylene glycol 200 will be present in the spray dilution in an amount of about 1.3 to 5% by volume and will be present in the adjuvant in an amount of about 10 to 50 parts per 100 parts coconut diethanolamide.

Another preferred hydrophilic agent is glycerin. Glycerin is water soluble and functions to improve water retention by the droplet and to solubilize the diethanolamide. Glycerin will generally be present in the spray dilution in an amount of about 0.6 to 6.6% by volume and will be present in the adjuvant in an amount of about 2 to 20% by volume. More preferably, the glycerin will be present in the spray dilution in an amount of about 1.3 to 5% and will be present in the adjuvant in an amount of about 10 to 50 parts per 100 parts coconut diethanolamide.

In addition to the foregoing, other agents and additives commonly used in agricultural sprays may be used in the adjuvant or spray compositions of the present invention including polyoxyethylenes, tallowamine ethoxylates, organosilicons, ethoxylated alcohols and polyvinyl alcohols. In particular, sticking agents such as water soluble polymers, latexes, crop oils, phthalic glycerol alkyd resins, di-l-p-menthene, etc., may be added.

The spray adjuvant of the present invention can be used in conjunction with substantially any aqueous agricultural spray formulation. It has been found to be particularly useful in the spray deposition of chlorothalonil in the control of black sigatoka (*Mycosphaerella fijiensis* var. difformis) in bananas. Other agricultural agents with which it could be used include fluazinum, zinc and manganese ethylene bis-dithiocarbamate, and other contact fungicides, herbicides, and insecticides.

The invention is illustrated in more detail by the following non-limiting example.

EXAMPLE

Application system: Air Tractor aircraft fitted with twelve (12) Micronair AU5000 rotary atomizers. Flying height 35 ft. and spray swath 80 ft. Flying speed approximately 130 mph.

Treatments:

1) Bravo 720* (2.0 l/ha) +Adjuvant** (1.0 l/ha).

2) Bravo 720* (2.0 l/ha).

* Chlorothalonil 54% formulation from ISK Biosciences, Inc., Mentor, Ohio
** The adjuvant contained 15% coconut diethanolamide, 5% glycerin and 5% polyethylene glycol (MW=200).

Fungicide application: Both treatments were applied as a commercial spray application utilizing the application system described above and according to the standard procedures. A total spray volume of 20 l/ha was applied. For both treatments, the aircraft sprayed in an alternating north-south direction. The conditions at the time of application are described in Table 1.

TABLE 1

Conditions at the time of each application.

| | Treatment 1 (Bravo + SA-21) | Treatment 2 (Bravo only) |
|---|---|---|
| Initial temperature | 76.5° F. | 77.0° F. |
| Final temperature | 77.0° F. | 79.0° F. |
| Start time application | 6:57 a.m. | 7:33 a.m. |
| Stop time of application | 7:10 a.m. | 7:59 a.m. |
| Weather | overcast | overcast |
| Windspeed | 0–1.00 m/s, NW | 0–1.00 m/s, NW |

Chlorothalonil sample collection: For each treatment, fifty (50) numbered, glass slides with a known surface area were placed 2 m apart on the ground in a line perpendicular to the flight path of the airplane. The slides were located in an open area between two sections of the banana plantation, such that the airplane passed directly overhead. The slides covered a horizontal distance of 98 m (321.6 ft), which is equivalent to four complete spray swaths. Upon completion of the fungicide application, the slides were allowed to dry and were collected and placed in plastic slide trays for storage until shipment.

Chlorothalonil analysis: The glass slides were analyzed for chlorothalonil deposits by gas chromatography. All data are reported in $\mu g/cm^2$ of chlorothalonil.

The main deposit of chlorothalonil on the glass slides for each treatment is shown in Table 2.

TABLE 2

Mean chlorothalonil deposited on glass slides ($\mu g/cm^2$).

| | Bravo 720 + Adjuvant | | Bravo 720 only | |
|---|---|---|---|---|
| Mean chlorothalonil deposit | 12.1 | a[1] | 9.4 | b |
| s (standard deviation) | 4.5 | | 5.8 | |
| n (sample size) | 50 | | 50 | |

[1]t-test: t = 2.62***
***significant (P = .01)

The mean chlorothalonil deposit for the Bravo+Adjuvant treatment was 12.1 $\mu g/Cm^2$ and the mean deposit was 9.14 $\mu g/cm^2$ for the treatment of Bravo 720 alone. The difference between mean deposits was highly significant (Table 2). For both treatments, chlorothalonil deposits were highest on slides that were directly under the flight path.

The adjuvant improved deposition of Bravo 720 in this trial. Mean chlorothalonil deposit was increased from 9.4 to 12.1 $\mu g/cm^2$, which represents a 29% increase in active ingredient deposit. In comparing treatments, chlorothalonil deposition in the overlap area (directly center relative to adjacent flight paths) was particularly improved. In the Bravo + adjuvant treatment, only two samples had less than 5 ug/cm$^2$ of chlorothalonil deposit, whereas in the Bravo only treatment, sixteen samples had less than 5 ug/cm$^2$ of chlorothalonil.

In this trial, the active ingredient of Bravo 720 (chlorothalonil) deposited on glass slides during a commercial application in a banana plantation was quantified. However, variables such as percent area covered and droplet spectrum were not measured. From visual observations of commercial applications of Bravo 720, the adjuvant appears to improve overall spray coverage and distribution on banana leaves.

Having described the invention in detail and by reference to preferred embodiments thereof, it will be apparent that modifications and variations are possible without departing from the scope of the invention defined in the appended claims.

What is claimed is:

1. A method for applying an agricultural agent to a crop comprising applying to a crop by spraying from an aircraft or a ground applicator a composition comprising water, an agricultural agent polyalkylene glycol, and coconut diethanolamide.

2. A method of claim 1 wherein the composition is applied to a crop by spraying from an aircraft.

3. The method of claim 2 wherein said agricultural agent is a herbicide, an insecticide or a fungicide.

4. The method of claim 3 wherein said composition additionally contains polyethylene glycol and glycerin.

5. The method of claim 3 wherein said diethanolamide is present in said composition in an amount of about 1.7 to 16.7% by volume.

6. The method of claim 5 wherein said composition additionally contains one or more hydrophilic agents.

7. The method of claim 6 wherein said hydrophilic agent is a polyalkylene glycol.

8. The method of claim 1 wherein said polyalkylene glycol is selected from the group consisting of polyethylene glycols 100, 200, 400, 600 and 1000 and said polyalkylene glycol is present in an amount of about 0.6 to 6.6% by volume.

9. The method of claim 8 wherein glycerin is present in the composition in the amount of about 0.6 to 6.6% by volume.

10. A spray adjuvant for addition to an agricultural composition to enhance spray deposition consisting essentially of an aqueous solution of coconut diethanolamide and one or more hydrophilic agents selected from the group consisting of polyalkylene glycol, glycerin and mixtures thereof.

11. The adjuvant of claim 10 wherein said hydrophilic agent is polyethylene glycol.

12. The adjuvant of claim 11 wherein said adjuvant additionally contains glycerin.

13. The spray adjuvant of claim 10 wherein a polyalkylene glycol is present in the composition and said polyalkylene glycol is selected from the group consisting of polyethylene glycols 100, 200, 400, 600 and 1000 and said polyalkylene glycol is present in an amount of about 10 to 50 parts per 100 parts coconut diethanolamide.

14. The spray adjuvant of claim 13 wherein glycerin is present in the composition in the amount of about 10 to 50 parts per 100 parts coconut diethanolamide.

15. A composition for aerial or non-aerial spray application to crops comprising water, an agricultural agent, polyalkylene glycol and coconut diethanolamide, said diethanolamide being present in an amount of about 1.7 to 16.7% by volume.

16. The composition of claim 15 wherein a polyalkylene glycol is present in the composition and said polyalkylene glycol is selected from the group consisting of polyethylene glycols 100, 200, 400, 600 and 1000 and said polyalkylene glycol is present in an amount of about 0.6 to 6.6% by volume.

17. The composition of claim 16 wherein glycerin is present in the composition in the amount of about 0.6 to 6.6% by volume.

* * * * *